(12) United States Patent
De Haas et al.

(10) Patent No.: US 7,804,597 B2
(45) Date of Patent: Sep. 28, 2010

(54) METHOD FOR MATCHING PAINT

(75) Inventors: Klaas Hendrik De Haas, Woerden (NL); Swie Lan Njo, Oegstgeest (NL); Eric Jacob Jan Kirchner, Leiden (NL); Roelof Johannes Baptist Gottenbos, Leiderdorp (NL)

(73) Assignee: AKZO Nobel Coatings International B.V., Arnhem (NL)

( * ) Notice: Subject to any disclaimer, the term of this patent is extended or adjusted under 35 U.S.C. 154(b) by 639 days.

(21) Appl. No.: 11/662,512

(22) PCT Filed: Sep. 16, 2005

(86) PCT No.: PCT/EP2005/054627

§ 371 (c)(1),
(2), (4) Date: Jun. 28, 2007

(87) PCT Pub. No.: WO2006/030028

PCT Pub. Date: Mar. 23, 2006

(65) Prior Publication Data

US 2007/0250273 A1 Oct. 25, 2007

(30) Foreign Application Priority Data

Sep. 17, 2004 (EP) .................... 04077584

(51) Int. Cl.
*G01J 3/46* (2006.01)

(52) U.S. Cl. .................. 356/402; 356/404; 356/407

(58) Field of Classification Search .................. 356/402, 356/405, 407; 345/589, 593, 597, 591, 604
See application file for complete search history.

(56) References Cited

U.S. PATENT DOCUMENTS

| 3,916,168 A | 10/1975 | McCarty et al. |
| 4,813,000 A | 3/1989 | Wyman et al. |
| 5,231,472 A | 7/1993 | Marcus et al. |
| 5,270,536 A | 12/1993 | Malhotra |

(Continued)

FOREIGN PATENT DOCUMENTS

EP 0 637 731 2/1995

(Continued)

OTHER PUBLICATIONS

Written Opinion of the International Search Authority, PCT International Patent Application No. PCT/EP2005/054627.

(Continued)

*Primary Examiner*—L. G Lauchman
(74) *Attorney, Agent, or Firm*—Kenyon & Kenyon LLP

(57) ABSTRACT

A method for matching colour properties and texture properties of a repair paint to colour properties and texture properties of a paint film on a substrate to be repaired is provided. In the method, the texture of the paint film is imaged with a digital imaging device, the imaged texture is analyzed using image analysis software, texture data is calculated, and the repair paint is formulated on the basis of the concentrations of paint modules, wherein each paint module is associated to specified texture data and colour data.

5 Claims, 2 Drawing Sheets

U.S. PATENT DOCUMENTS

Figure 1:
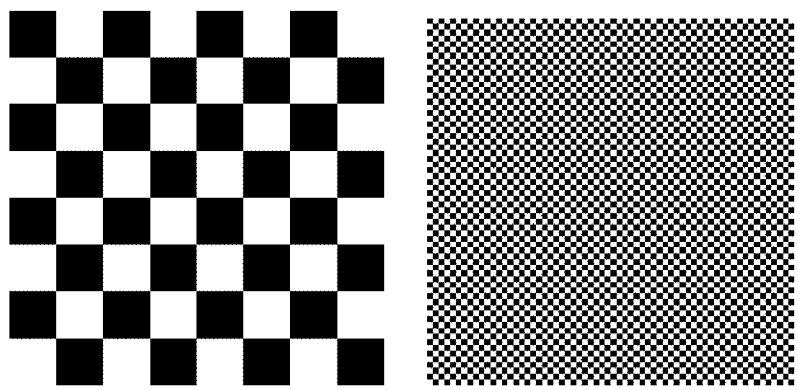

| | | | |
|---|---|---|---|
| 6,064,487 A | 5/2000 | Kettler et al. | |
| 6,741,260 B2 * | 5/2004 | Hirayama et al. | 345/589 |
| 6,744,513 B2 * | 6/2004 | Kubo et al. | 356/402 |
| 6,750,970 B2 * | 6/2004 | Masuda | 356/402 |
| 6,959,111 B2 * | 10/2005 | Hirayama et al. | 382/167 |
| 7,145,566 B2 * | 12/2006 | Karlov | 345/530 |
| 7,248,350 B2 * | 7/2007 | Kettler | 356/128 |
| 2001/0036309 A1 | 11/2001 | Hirayama et al. | |
| 2003/0156752 A1 * | 8/2003 | Turpin et al. | 382/162 |
| 2003/0208345 A1 | 11/2003 | Anderson | |
| 2005/0018191 A1 * | 1/2005 | Luo et al. | 356/404 |

FOREIGN PATENT DOCUMENTS

| | | |
|---|---|---|
| EP | 0 932 038 A1 | 7/1999 |
| WO | WO 01/25737 | 4/2001 |
| WO | WO 03/083420 | 10/2003 |

OTHER PUBLICATIONS

International Search Report, PCT International Application No. PCT/EP2005/054627.

Press et al., William H., "Numerical Recipes in Pascal," *The Art of Scientific Computing*, Cambridge University Press, 1989.

Hardy, J., "How Large is a Point Source?" *Journal of the Optical Society of America*, vol. 57, No. 1, Jan. 1967.

Levine, Michael W., *Fundamentals of Sensation and Preception*, 3$^{rd}$ Edition, Oxford University Press, New York, 2000.

Judd et al., Deane B., "Physics and Psychophysics of Colorant Layers," *Color in Business, Science, and Industry*, 2$^{nd}$ Edition, 1975.

Search Report, European Patent Application No. 04077584.3, dated Jan. 24, 2005.

* cited by examiner

METHOD FOR MATCHING PAINT

FIELD OF THE INVENTION

The present invention relates to a method for matching of a repair paint to texture properties, and optionally colour, of a paint film on a substrate to be repaired.

BACKGROUND OF THE INVENTION

Repairing painted surfaces requires that the repair paint visually matches the originally applied paint film. To this end, the colour of the original paint film is measured and subsequently a paint composition is determined having substantially the same colour within a predetermined tolerance. This can be done by searching a suitable paint composition in a databank or a suitable paint composition can be calculated based on the colorimetric data of the paint components.

To allow easy formulation of matching paints in any colour, toners are often used. Toners are compositions of base colours comprising all ingredients which make up a complete paint. These toners can be mixed to obtain a paint of a colour, which after being applied and dried as a paint film, matches the colour of the paint originally coating the substrate. Based on the colorimetric data of the individual toners, the colorimetric features of mixtures can be predicted by calculation, taking into account the concentrations of the toners used. Alternatively, paint compositions can be formulated on basis of other types of modules, such as pigment concentrates, binder modules, effect modules, components comprising flop-controllers, etc.

Besides colour, a paint film shows numerous further visual properties. Particularly when effect pigments, such as for example aluminum flake pigments or pearlescent pigments, are used, the look of a paint film is not of a uniform colour, but shows texture. This can include phenomena as coarseness, glints, micro-brilliance, cloudiness, mottle, speckle, sparkle or glitter. In the following, texture is defined as the visible surface structure in the plane of the paint film depending on the size and organization of small constituent parts of a material. In this context, texture does not include roughness of the paint film but only the visual irregularities in the plane of the paint film. Structures smaller than the resolution of the human eye, contribute to "colour", whereas larger structures generally also contribute to "texture".

Also particles which are not directly observable by themselves, can contribute to the overall visual appearance of a paint film. Des-orienters are an example of such particles. Effect pigments are generally flakes tending to take a horizontal orientation in a cured film. To prevent this, and to obtain more variation in flake orientation, spherical particles are used, referred to as des-orienters. Using des-orienters in a metallic paint, results in more glitter.

Hitherto, the texture of the paint film to be repaired was judged by the eye, e.g., by comparing it with samples on a sample fan. The results of such approach are strongly dependent on the skills of the practitioner and are often not satisfying.

In practice, a colour specialist wanting to match a textured paint, first selects one or more effect modules or toners to obtain a matching texture effect. Meanwhile or subsequently, colourant modules or toners are selected to obtain a colour match. The result is compared with the original paint and iteratively adjusted if correction appears to be necessary. Selecting the right effect modules is difficult and requires a trial and error approach or accurate computer analysis of the effect pigments in the paint to be matched.

EP-A 637 731 discloses a method for reproducing texture properties of a paint film. The reproduced paint is formulated on basis of concentrations of paint modules. The formulation is selected from a database or formulations with given texture properties. If this does not result in a satisfying match, corrections can be made by interpolation between two close matches.

WO 01/25737 discloses a method of combined colour and texture matching, using a digital imaging device, such as a CCD camera, to determine the texture.

A matching paint is determined by searching in a databank of colour formulations linked to texture data.

US 2001/0036309 discloses a method of measuring micro-brilliance and using it for matching a repair paint with an original paint on, e.g., an automobile. The method includes measurement of colour as well as micro-brilliance, a specific type of texture. A colour formula with a matching micro-brilliance is selected from a databank of paint formulas. Consequently, the obtained micro-brilliance texture is acceptably matching. However, the colour is not necessarily matching evenly well. Hence, the colour formula needs to be iteratively adjusted until the colour match is also acceptable. In this prior art system, colour formulas that initially do not have the right texture are not taken into consideration, although these formulas could still be viable candidates as a formulation to start with. Furthermore, this prior art method does not assure that the texture remains intact during the adjustments of the colour formulas.

SUMMARY OF THE INVENTION

The object of the invention is to improve matching of repair paints with paint originally applied on a substrate to give more accurate results in a faster and more reliable way, preferably without the need to build up a database of complete formulations with specified texture data.

The object of the invention is achieved by a method for matching a repair paint to texture properties of a paint film on a substrate to be repaired, the repair paint being formulated on basis of concentrations of paint modules characterized in that each paint module is associated to specified texture data, and in that a calculational texture model using the texture date of the paint modules to calculate a repair paint with matching texture properties.

These texture data can for instance include the particle size distribution of the effect pigments in the toner, and the optical contrast, defined as the difference in lightness, between the effect pigment and the other toner pigments present in the toner.

Surprisingly it was found that a matching texture can be obtained by mixing toners selected from a limited range of toners showing particular pre-determined texture parameters, and that a computer can be used to calculate a matching mixture of texture toners.

Preferably, the paint is also matched with the colour properties of the original paint. It has unexpectedly been found that by simultaneously matching colour and texture, the overall visual match appears to be improved, even if the colour match per se is a bit less.

An alternative embodiment of the present invention, involves using a database of colour formulations, from which a best match is selected which subsequently further optimized using the calculation texture model by adapting the toner concentrations to obtain a closer texture match or combined colour and texture match. The adaptations can be small or can require removal of one or more toners or adding one or more new toners to the selected formulation.

The invention also relates to a method for repairing a paint film on a substrate and to a method for matching of a repair paint to texture properties of a paint film on a substrate to be repaired using paint modules with specified texture data, which are used to calculate a combination of paint modules matching the required texture properties, mixing the modules as calculated and applying the resulting paint on the substrate to be refinished. This embodiment enables automated selection of effect toners, which was not possible hitherto. As a result, no inherently inaccurate visual assessment of a colour specialist is required.

Texture can be imaged by means of a digital imaging device, such as a CCD camera. Subsequently, image analysis software can be used to translate the image into one or more texture parameters. Suitable image processing software is for instance Optimas or Image ProPlus, both commercially available from Media Cybernetics, MacScope, available from Mitani Corporation, or Matlab, available from The MathWorks Inc.

DETAILED DESCRIPTION OF THE INVENTION

Measuring Texture

In order to extract a texture parameter from a digital image, a set of representative car colours is collected and judged visually using a reference scale that covers the whole texture parameter range. An algorithm is derived that extracts texture parameter values from the images of the set of car colours that closely correlate to the visual assessments.

The texture parameter "coarseness" describes the visual surface roughness of a sample: a coating shows coarseness when it exhibits a clear pattern of dark and light areas. Not only the ratio between dark and light areas, which for a black and white image can be expressed in a gray value standard deviation, is of importance, but also the size of the areas. For example, the drawings in FIG. 1 have the same gray value standard deviation, but clearly differ in pattern.

To extract coarseness, the following algorithm can be used:

Take a CCD image of N×N pixels. The gray value standard deviation GVSTD is determined at several scales X: At the smallest scale X=1 it is calculated per individual pixel. At the second smallest scale it is calculated over the average gray values of squares of 2×2 pixels (X=4). At the third smallest scale squares of 4×4 pixels are used, so X=16. This is repeated up to the maximum scale of N×N pixels (X=N$^2$).

The gray value standard deviation GVSTD can be described as a function of the scale X using:

$$GVSTD = A + \frac{B}{X^C} \quad (1)$$

With GVSTD and X being known, parameters A, B, and C can be calculated by fitting.

The A, B and C parameters can be correlated to a visual coarseness value VC by:

$$VC = \alpha_1 + \alpha_2 * A + \alpha_3 * B + \alpha_4 * C \quad (2)$$

The values for the $\alpha_1$, $\alpha_2$, $\alpha_3$ and $\alpha_4$ have been pre-determined before by comparison with a set of panels of representative car colours. These reference colours are judged by the eye and accorded a value according to a reference scale. Judging is done by a number of people and the accorded values are averaged per panel. For each of these reference colours, the measured VC should be equal to the value according to the reference scale for visual judgment. The parameters $\alpha_1$, $\alpha_2$, $\alpha_3$ and $\alpha_4$ are found by minimizing the difference between observed and measured values for all used panels in the set of representative car colours. To find equal values for the $\alpha_1$, $\alpha_2$, $\alpha_3$ and $\alpha_4$ parameters for all panels of the set of representative car colours, the square value of the difference between the reference scale value and the visual coarseness value VC is calculated for each panel. The sum of all these square values $\Sigma_{all\ panels}$ (visual judgment$_{panel\ i}$−VC$_{panel\ i}$)$^2$ is subsequently minimized, resulting in values for $\alpha_1$, $\alpha_2$, $\alpha_3$ and $\alpha_4$. With these parameters being known, the coarseness of any car paint film can be determined.

The aforementioned method to correlate the coarseness to visual assessments by using the theoretical model (2) can be done in general for any texture parameter for any observation and illumination condition for any particular model. This particular model can include any physical parameter (like particle size, flake composition, etc.), colour parameter (like CIE Lab parameters, etc.) or image parameters (like grey value standard deviation, etc.).

An alternative way to measure texture, in particular so-called micro-brilliance, with a digital imaging device and image analysis software is disclosed in US 2001/0036309, herein incorporated by reference.

The parameter 'glints' is another texture parameter, which describes the perception of bright tiny light spots on the surface of an effect coating under directional illumination conditions that switch on and off when you change the viewing angle. Glints is best observed in direct sun light, i.e. with a cloudless sky, from less than one meter. Even when the observation conditions are the same, some effect coatings show many bright glints, whereas other effect coatings show few or even no glints at all. A glint scale has been designed with which an observer can visually inspect the effect coating, and express the glints aspect as a number. Some effect coatings will have a small glints value, others a large glints value. In this way, the texture aspect "glint" of a coating can be observed in a quantitative way.

The texture parameter "glint" can be described more specifically by making the distinction between glint intensity and glint size. Glint intensity is the light intensity or light intensity distribution of the bright tiny light spots. Glint size is the area or area distribution of the spots.

A second way to make a further distinction between glints is by their colour or colour distribution.

A glint is visible only in a given range of mutual orientations of illumination direction, observation direction and sample orientation. As a consequence, a third way to characterize glints is to determine the range of illumination angles (or the distribution thereof) for which a glint is visible to the human eye, given a certain observation angle and sample orientation. Similarly, the range of observation angles (or the distribution thereof) for which a glint is visible to the human eye can be used given a fixed illumination angle and sample orientation, or the range of sample orientations (or the distribution thereof) for which a glint is visible to the human eye, can be used given a fixed observation angle and a fixed illumination angle.

Measuring Colour

Generally, texture matching will be combined with colour matching. To match a colour, the colour has to be measured first. Colours can be measured with the aid of colour meters, such as spectrophotometers or tri-stimulus meters. The measured signals can be used for the determination of a paint formula with a matching colour. US patent application US 2001/0036309 describes a method of measuring colour with the aid of a multi-angle spectrophotometer and using the measured data to search for a colour formula in a databank. U.S. Pat. No. 4,813,000 discloses measuring a selected colour with the aid of a tri-stimulus colour analyser and using the measured chromaticity data to search for a colour formula in a databank. WO 01/25737 discloses how to measure colour with a digital imaging device such as a scanner or a digital camera.

After measuring the texture properties, and optionally also the colour, a matching paint formulation is calculated. To this end, the texture, and optionally colour, of paint formulations is predicted.

Predicting Texture on Basis of Concentrations of Paint Modules

A suitable repair paint is formulated as a mixture of a number of paint modules, e.g., toners, selected from a set of modules. Texture parameters of the modules have been pre-determined. Based on these parameters, a mixture can be calculated showing a desired texture parameter. This way, a formulation for a repair paint can be calculated having a texture which closely matches the texture of the original paint film.

The texture of a colour formula can be expressed in visual texture properties like coarseness, sparkling, glints, or micro-brilliance, but also in physical texture properties like particle size, particle size distribution, particle shape, particle colour, and the number of particles, a particle being, e.g., an effect pigment, or a couple of effect particles which cannot directly be distinguished visually or in the image, such as de-ori-enters.

A texture parameter T of a single colour formula containing V toners each having a texture property $c^j$ can be written as:

$$T_i = (c^1, c^2, \ldots, c^v) \quad (3)$$

$T_i$ is preferably a visual property, like coarseness, but could also be a physical texture property. For example, a coarseness model for a formulation of a number of v toners could be written as a function of Kubelka-Munk k and s values and the toner concentrations c, measured an optical geometry g and wavelength $\lambda$:

$$T_{coarseness} = (k^1_{\lambda g}, k^2_{\lambda g}, \ldots, k^v_{\lambda g}, s^1_{\lambda g}, s^2_{\lambda g}, \ldots, s^v_{\lambda g}, c^1, c^2, \ldots, c^v) \quad (4)$$

In this example, the coarseness model uses the same parameters as the colour model (K and S values). This is not always necessary for texture models: a more generic example shows that $T_i$ could be dependent on specific texture properties of the toners:

$$T_{coarseness} = (A^1, A^2, \ldots, A^v, B^1, B^2, \ldots, B^v, c^1, c^2, \ldots, c^v) \quad (5)$$

where $A^j$ is for example the particle area or area distribution of the specific toners, and $B^j$ is the particle shape (e.g. major axis length or circularity) of the specific toners. $T_i$ can be a visual property like coarseness $T_{coarseness}$, but can also be, e.g., the overall particle area or area distribution of the colour formula or the overall particle shape in the colour formula.

The texture of a standard paint, e.g., the paint for a car to be repaired, can be expressed in a number texture parameters $T_i^{ST}$. When the texture of this standard paint is to be matched, calculational methods such as for example the least squares method can be used to minimize the following expression by changing the toner concentrations:

$$X^2 = \sum_{i=1}^{I} \{T_i(c^1, c^2, \ldots, c^v) - T_i^{ST}\}^2 \quad (6)$$

by using a non-linear optimization algorithm like the Marquardt-Levenberg algorithm (as described in Numerical Recipes in Pascal, W. H. Press, B. P. Flannery, S. A. Teukolsky, and W. T Vetterling. Cambridge University Press, 1989). This means that for a single paint formula the toner concentrations are varied in such a way that the theoretical texture differences between the colour formula and a specified target colour is minimized (i.e. $X^2$ from equation (6) is minimized).

Coarseness

The following is an example of a calculational model for predicting the coarseness of a paint film based on pre-determined coarseness data of paint modules used to formulate the paint. The following general function can be defined to predict the coarseness of a calculated colour formula as the sum of a number of predictors x, each with a weigh factor $\beta$:

$$F = \Sigma \beta_i * x_i \quad (7)$$

A possible predictor x is for instance the concentration of a toner used in the colour formulation. In Table 1 an example of a colour formula is given:

TABLE 1

| Toner | Concentration |
|---|---|
| Q065 (pigment free binder module) | 0.23 |
| Q110 (toner with a solid pigment) | 0.17 |
| Q160 (toner with a solid pigment) | 0.20 |
| Q811E (toner wit metallic pigment) | 0.30 |
| Q811U (toner wit metallic pigment) | 0.05 |
| Q951F (toner wit pearlescent pigment) | 0.05 |

Three Possible Predictors x are:

CONCS=Concentration Solids: 0.17+0.20

CONCM=Concentration Metallics: 0.30+0.05

CONCP=Concentration Pearls: 0.05

In this case, the predictors relate to toner types (solids, metallics, pearlescents, etc.). Alternatively, predictors can be used relating to individual toners, but this would generally result in a very large number of predictors. Another option is to use predictors relating to concentrations of solids with a low scattering coefficient (CONCSL), solids with a high scattering coefficient (CONCSH), fine metallics (CONCMF), medium metallics (CONCMM), coarse metallics (CONCMC), pearlescents with a low scattering coefficient (CONCPL), pearlescents with a high scattering coefficient (CONCPH), des-orienter (CONCQ), etc.

It was found that scattering is a good indicator for coarseness. To avoid too many predictors, one can take the sum over the colourant concentrations times the colourant scattering coefficients averaged over the 16 wavelengths at 25°, 45° and 110°. For the metallics in this case this would be for 25°:

$$SUMMS1 = 0.30 * AverageS_{25}Q811E + 0.05 * AverageS_{25}Q811U \quad (8a)$$

And for the other angles:

$$SUMMS2 = 0.30 * AverageS_{45}Q811E + 0.05 * AverageS_{45}Q811U$$

$$SUMMS3 = 0.30 * AverageS_{110}Q811E + 0.05 * AverageS_{110}Q811U$$

Wherein "AverageS$_{25}$Q811E" is the average value of the scattering coefficient over the 16 wavelengths at 25° for toner Q811E and "AverageS$_{25}$Q811U" is the average value of the scattering coefficient over the 16 wavelengths at 25° for toner Q811U, weighed by their respective concentrations as shown in Table 1.

The same can be done for the absorption coefficient. For the metallics in this case this would be for 250:

$$\text{SUMMK1} = 0.30 * \text{Average} K_{25} Q811E + 0.05 * \text{Average} K_{25} Q811U \tag{8b}$$

The predictors SUMMS1, SUMMS2, SUMMS3, SUMMK1, SUMMK2, and SUMMK3 are used in equation (7).

Additionally or alternatively, the L, a, b, Munsell chroma and Munsell hue values of the colour at the three angles can be used as predictor. Other predictors that can be thought of are ratio S to K and vice versa, splitting the wavelength domain into two (SUMMS1A and SUMMS1B) or four (SUMMS1A, SUMMS1B, SUMMS1C and SUMMS1D) parts instead of averaging over the whole range, and defining a sort of contrast predictor ($[\text{constant} - \{S/K\}_{solid}]/\{S/K\}_{solid}$). The number of possible combinations seems countless; however, many are highly correlated.

Generally a number of 6 coarseness classes or categories are defined. Because these categories are used, a logistic regression is applied to predict the coarseness instead of a linear model, the latter would suggest a continuous scale. The function can be written as:

$$\ln\left(\frac{p(y \leq y_i)}{(1 - p(y \leq y_i))}\right) = \alpha_i + F, \quad i = 1\ldots 5 \tag{9}$$

with $\alpha$ being the boundaries between categories.

Figure 2:
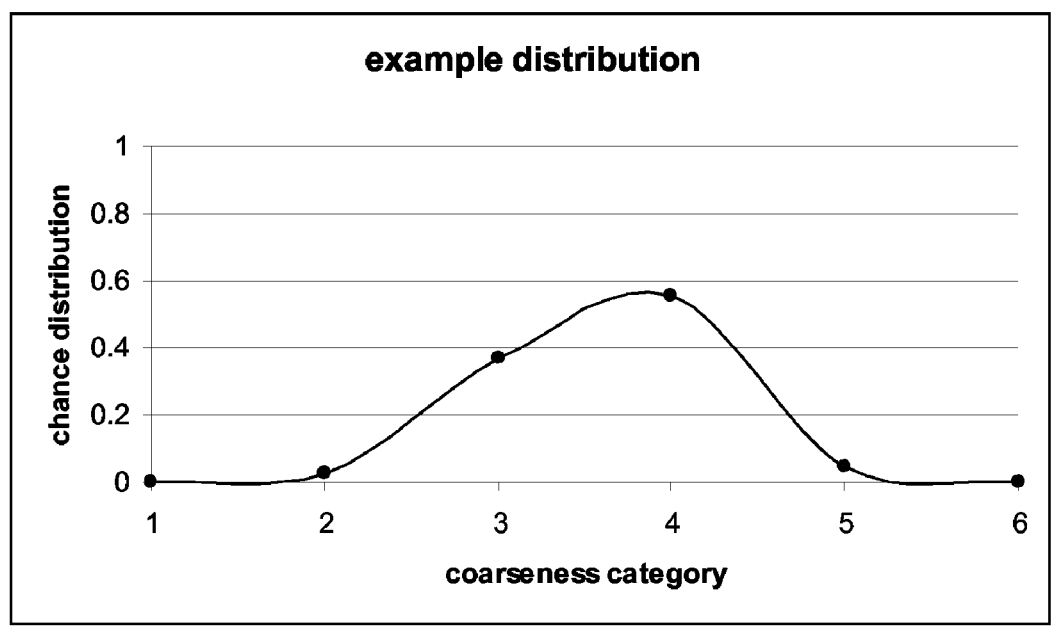

The chance on a certain coarseness value can be calculated as follows:

$P(\text{coarseness value} = 1) = p(y \leq y_1)$ $P(\text{coarseness value} = 2) = p(y \leq y_2) - p(y \leq y_1)$ $P(\text{coarseness value} = 3) = p(y \leq y_3) - p(y \leq y_2)$ $P(\text{coarseness value} = 4) = p(y \leq y_4) - p(y \leq y_3)$ $P(\text{coarseness value} = 5) = p(y \leq y_5) - p(y \leq y_4)$ $P(\text{coarseness value} = 6) = 1 - p(y \leq y_5)$ FIG. 2 shows an example of a chance distribution. As coarseness value either the median, mode or $\Sigma i * P(i)$ with $i=1$ to 6 is taken.

The values for the $\alpha$'s and $\beta$'s are pre-determined by comparison with a set of panels of representative car colours. These reference colours are judged by the eye and accorded a value according to a reference scale. This is done by a number of people and the accorded values are averaged per panel. For each of these reference colours, the predicted coarseness value should be equal to the value according to the reference scale for visual judgment. The parameters are found by minimizing the difference between observed and measured values for all used panels in the set of representative car colours. With these parameters being known, the coarseness of any car paint film can be predicted.

Glints

A glints model has been designed in order to predict the glint number of an effect coating, based on only the concentrations of the various toners used in the paint. The model may be used when trying to match an original colour, e.g., of a car to be refinished. In that case, the model can make sure that also the glint aspect of the original car colour is matched.

In order to make these predictions, the glint model requires a number of input parameters:

the illumination and observation angles. This means the angle from which the light source (for example, the sun) is shining on the coating, and the angle at which the observer is looking to it. Also the distance from which the light source is shining, and the distance between observer and coating are relevant. The intensity of the light source is also needed. And finally, the angular scope of detector/observer's eye and light source, as seen from the coating.

Sizes and thicknesses and number of flake particles inside effect toners.

The orientations in which the flakes for each toner are lying in a coating

The absorption and scattering (K&S) values of the non-effect toners, and the refractive index of the non-effect toners. These are used to calculate how the coating absorbs light.

First the colour and intensity of the background, i.e. the coating surrounding glints, are calculated. This is important, because the human eye can detect a tiny light source like a glint better when it has a dark surrounding than when it has a lighter surrounding. The background colour is calculated based on the absorption and scattering (K&S) values of the non-effect toners, under the assumption that all light falling on an effect coating is either absorbed or reflected by a flake at some depth in the coating. The various contributions from flakes at several depths in the coating are all taken into account.

After calculating the background colour and intensity, it is calculated how intense a glint should be, in order to make it visible for the human eye, against the calculated background. The calculation is done as described in the article of hardy, J. Opt. Soc. Am 57 (1967) 44-47. Next, it is calculated how many flakes under one square centimeter of coating surface have the right orientation and depth in the coating, such that the light reflected from them is intense enough to be visible against the background. This number is called N and is found by multiplying four terms. The first term accounts for the fact that glints are more easily recognizable against a darker background, and deals with light absorption by solid pigments. The second term accounts for the dependence on viewing/illumination angle. The third term accounts for the concentration of flakes in the coating, and the fourth term calculates the fraction of flakes that have the correct orientation in order to make them visible as glint.

Now using the psychologically based Weber law that human perception is often based on the logarithm of stimulus, the logarithm of N is correlated with the visually observed glint scale numbers. The Weber law is described in M. W. Levine, Fundamentals of Sensation and Perception, 3 ed., Oxford University Press, New York, 2000. Now using the psychologically based Weber law that human perception is often based on the logarithm of stimulus, the logarithm of N is correlated with the visually observed glint scale numbers.

Matching Colour on Basis of Concentrations of Paint Modules

Colour formulas can be determined in a number of ways, i.e. by means of search procedures, calculations, or combinations of the two. For example, use may be made of a databank comprising colour formulas having colorimetric data linked thereto. Using the calculated colorimetric data of the measured selected colour, the most closely matching colour formula can be found. Alternatively, it is possible to use a databank having colour formulas with spectral data linked thereto. Known calculation methods can be used to calculate the colorimetric data of the colour formulas and compare them. Also, a databank can be used in which the absorption and reflection data, the so-called K and S data, of pigments are stored. Using K and S data in combination with pigment concentrations makes it possible to calculate the colour formula of which the colorimetric data most closely match the colorimetric data of the measured selected colour. The methods in question have been described in detail in D. B. Judd et al., *Colour in Business, Science and Industry*. It is possible to combine the aforesaid search and calculation methods.

Colour can be expressed by the paint film reflection as a function of wavelength of visible light. Alternatively, colour can be expressed in accordance with the so-called CIE Lab system, as defined by the Commission International d'Eclairage, or similar systems, such as the CIE Luv, CIE XYZ systems or the Munsell system. In paint films comprising effect pigments, the measured reflection R is dependent on the optical geometry, which is defined by the angle of observation and the angle of illumination. The theoretical reflection $R_{g\lambda}$ at a wavelength $\lambda$ and at optical geometry g of a colour formulation composed by a number of v toners, can be written as a function of the colorimetric parameters c of each toner:

$$R_{g\lambda} = (c^1, c^2, \ldots c^v) \quad (10)$$

Alternatively, the L,a,b values of a paint formula can be written in a similar way.

This colour formula contains V toners, g measuring geometries, and $\lambda$ wavelengths per geometry. Generally, g=1 in case of solid colours without effect pigments, and $\lambda$=16 when the wavelength range is between 400 and 700 nm and the wavelength interval is 20 nm. For paints comprising effect pigments, g is usually about 3.

In accordance with the Kubelka Munk model (the hiding version) the reflection $R^{KM}$ is defined by the following formula:

$$\frac{\sum_{i=1}^{V} c_i \cdot K_{g\lambda}^i}{\sum_{i=1}^{V} c_i \cdot S_{g\lambda}^i} = \frac{(1 - R_{g\lambda}^{KM})^2}{2 R_{g\lambda}^{KM}} \quad (11)$$

in which $K^i_{g\lambda}$ is the absorption factor at wavelength $\lambda$ and optical geometry g of toner i and $S^i_{g\lambda}$ is the scattering factor at wavelength $\lambda$ and optical geometry g of toner i. Hence, a similar formula as equation (4) is obtained:

$$R_{g\lambda}(K^1_{g\lambda}, K^2_{g\lambda}, \ldots, K^V_{g\lambda}, S^1_{g\lambda}, S^2_{g\lambda}, \ldots, S^V_{g\lambda}, c^1, c^2, \ldots, c^v) \quad (12)$$

In order to match a standard colour (e.g. the colour of the car to be repaired) expressed in reflection values $R^{ST}_{g\lambda}$, for example the least squares method can be used to minimize the following expression:

$$X^2 = \sum_{g=1}^{G} \sum_{\lambda=1}^{\Lambda} \{R_{g\lambda}(c^1, c^2, \ldots, c^v) - R^{ST}_{g\lambda}\}^2 \quad (13)$$

by using a non-linear optimization algorithm like the Marquardt-Levenberg algorithm. This means that for a single colour formula the toner concentrations are varied in such a way that the theoretical colour difference between the colour formula and a specified target colour is minimized (i.e. $X^2$ from equation (13) is minimized). The concentrations $c^i$ of V different toners in one colour formula are estimated by fitting the $c^i$ parameters in the following equation using fixed K and S values for each toner:

$$R_{g\lambda}(\text{fit parameters:} c^1, c^2, \ldots, c^V; \text{fixed:} K^1_{g\lambda}, K^2_{g\lambda}, \ldots, K^V_{g\lambda}, S^1_{g\lambda}, S^2_{g\lambda}, \ldots, S^V_{g\lambda}) \quad (14)$$

This way of representing colour formulation also incorporates the cases for which toners are omitted from or added to a colour formula: this can be achieved by setting the accompanied toner concentrations to zero, or removing the parameter respectively.

Combined Colour and Texture Matching

The preferred way to cope with texture parameters is to match a paint based on colour and texture simultaneously. To this end, a combined colour and texture model "RT" has to be defined. This can for example be done by combining equations 6 and 13, i.e. by adding them up and defining a weigh factor $\alpha$, ranging between 0 and 1:

$$X^2 = (1 - \alpha) \cdot \sum_{g=1}^{G} \sum_{\lambda=1}^{\Lambda} \{R_{g\lambda}(c^1, c^2, \ldots, c^v) - R^{ST}_{g\lambda}\}^2 + \alpha \cdot \sum_{i=1}^{I} \{T_i(c^1, c^2, \ldots, c^v) - T^{ST}_i\}^2 \quad (15)$$

Equation (15) is minimized by using a non-linear optimization algorithm like the Marquardt-Levenberg algorithm. The fit parameters are the toner concentrations, and the fixed parameters are the K and S values from the colour model and the texture parameters from the texture model.

The weigh factor $\alpha$ can be used to set the priority between colour and texture. If the colour match is given more priority than the texture match, then $\alpha$ is less than 0.5, while if the texture match is given more priority, then $\alpha$ is more than 0.5. The higher the value of $\alpha$, the more important the role of texture. The factor $\alpha$ can be kept constant for all colour formulas, but can also be varied for each separate colour formula.

An alternative way to deal with texture is using texture as a constraint during a more or less standard colour formulation. This means that equation (13) is solved instead of equation (15), but during the estimation the toner concentrations are not allowed to vary in such a way that the texture parameter differences $T_i(c^1, c^2, \ldots, c^v) - T^{ST}_i$ exceed predetermined upper and lower limits.

Figure 3:
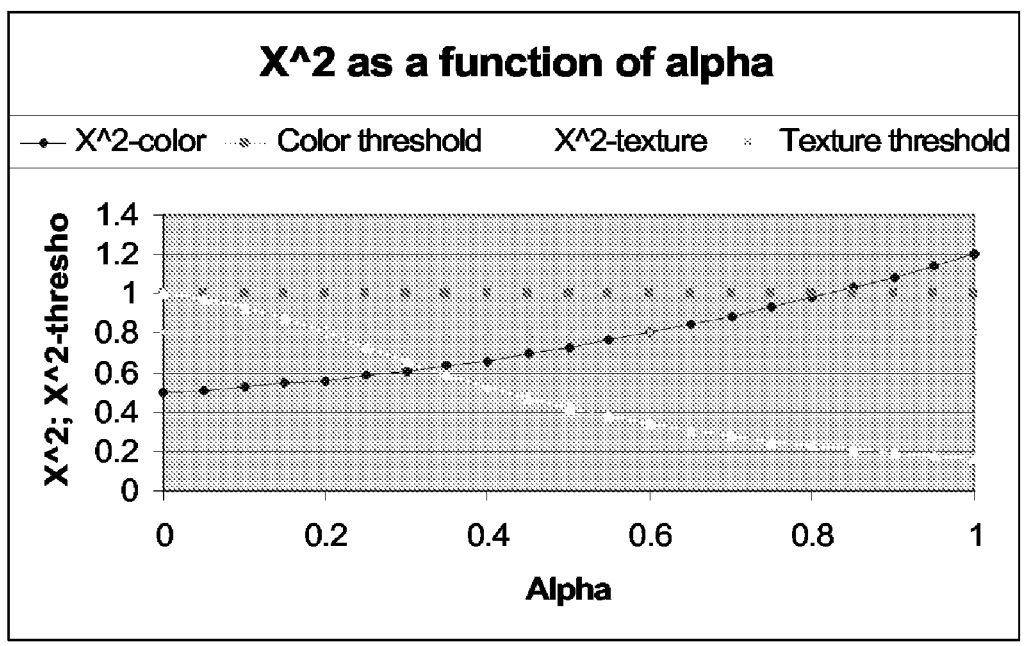

FIG. 3 shows a schematic example how to use equation (15), dividing $X^2$ in a colour part and a texture part:

$$X^2 = (1-\alpha) \cdot X_{Color}^2 + \alpha \cdot X_{Texture}^2 \quad (16)$$

FIG. 3 shows graphically the function of equation 16 for a specific colour formula. When the formula is matched on colour only ($\alpha$=0) then $X^2_{colour}$ (dark blue line) is in this particular case lower than the colour acceptance threshold (pink line) which means that the colour is visually acceptable according to the average colour specialist. However, $X^2_{texture}$ (yellow line) is quite large and in this particular case larger than the texture threshold (cyan line), which means that the texture is visually not acceptable for the average colour specialist. When, on the other hand, a match is based on texture only ($\alpha$=1) then the colour is not acceptable while the texture is acceptable. To obtain a satisfactory match, both $X^2_{colour}$ and $X^2_{texture}$ must be lower than the corresponding thresholds. This is achieved in this particular example when $0.2 \leq \alpha \leq 0.6$. It is emphasized that this is just an example. There will always be colour formulas for which either the colour and/or texture will or cannot become lower than their visual thresholds. This is for example the case when the toners have not been selected correctly.

There are different ways to deal with the weighing factor α. One way is to set α to a fixed value that on average enables the best combined colour and texture match. A more preferred way is to determine an optimum value α specifically for each separate colour formula.

The invention is further explained by the following example.

Example

A dark gray effect coating ("standard") was measured at three angles (25°, 45° and 110°) with a ColourChecker. Table 2 shows the measurement results.

TABLE 2

| | "Standard" | | |
|---|---|---|---|
| | $L^*$ | $a^*$ | $b^*$ |
| 25° | 26.71 | −1.57 | −4.59 |
| 45° | 10.73 | 0.9 | −2.54 |
| 110° | 4.62 | 1.73 | −0.44 |

As texture property the coarseness was measured and indexed at 0.91.

An effort was made to match on colour only ("colour") and on colour and texture ("coltex"). For both calculations the same set of colourants was used. Recipes were sprayed out and samples measurements. Recipes are given in Tables 3, colour measurements results in Tables 4 and 5. For "colour" the coarseness value was 2.24 and for "coltex" 1.23, coarseness differences with the standard are given in Table 6.

TABLE 3

| | Recipes "Colour" and "ColTex" | |
|---|---|---|
| Colourant | "Colour" Amount (part by weight) | "ColTex" Amount (part by weight) |
| Toner A | 3.22 | 2.85 |
| Toner B | 47.92 | 53.30 |
| Toner C | 3.00 | 0.00 |
| Toner D | 4.39 | 5.82 |
| Toner E | 15.07 | 13.52 |
| Toner F | 12.89 | 11.39 |
| Toner G | 7.87 | 8.06 |
| Toner H | 5.64 | 5.07 |

TABLE 4

| | "Colour" | | |
|---|---|---|---|
| | $\Delta L^*$ | $\Delta a^*$ | $\Delta b^*$ |
| 25° | −0.56 | −0.31 | 0.01 |
| 45° | 0.09 | −0.24 | −0.02 |
| 110° | 0.21 | 0.11 | 0.36 |

TABLE 5

| | "ColTex" | | |
|---|---|---|---|
| | $\Delta L^*$ | $\Delta a^*$ | $\Delta b^*$ |
| 25° | −0.58 | −0.75 | −0.35 |
| 45° | 0.2 | −0.46 | −0.3 |
| 110° | 0.23 | −0.11 | 0.03 |

TABLE 6

| ΔCoarseness "Colour" and "ColTex" (criterion ΔCoarseness ≦ 0.8) | | |
|---|---|---|
| | "Colour" | "ColTex" |
| ΔCoarseness | 1.33 | 0.32 |

Using the weight averaged ΔEcmc (WADE), "colour" scores 0.46 and "coltex" 0.68. This example shows the added value of texture matching: the texture of "coltex" matches the texture of "standard", is a bit more off in colour than "colour", but satisfies the requirement WADE<1.

The invention claimed is:

1. A method for matching a repair paint to texture properties and colour properties of a paint film on a substrate to be repaired, the method comprising:
   imaging a texture of the paint film with a digital imaging device;
   analyzing the imaged texture using image analysis software;
   calculating texture data; and
   formulating the repair paint on the basis of concentrations of paint modules, wherein each paint module is associated to specified texture data and colour data, and wherein a calculational texture and colour model using the texture data and colour data of the paint modules is used to calculate a repair paint with matching texture and colour properties, and wherein a colour and texture difference formula is used that combines a colour difference formula and a texture difference formula with a weighing factor, wherein an optimum value for the weighing factor is determined specifically for each separate colour formula.

2. The method according to claim 1, wherein a spectrophotometer is used to measure the colour of the paint film.

3. The method according to claim 1, further comprising calculating the concentrations of a given set of paint modules required to match a specified texture, and mixing the given set of paint modules with further modules.

4. The method according to claim 1, wherein, for the color to be repaired, the paint modules are selected without the need of a visual assessment of the to be repaired color.

5. The method according to claim 1 wherein the digital imaging device is a CCD camera.

* * * * *